(12) United States Patent
Gandy et al.

(10) Patent No.: US 8,871,526 B1
(45) Date of Patent: Oct. 28, 2014

(54) APPARATUS FOR OBTAINING GROWTH FACTORS

(71) Applicant: Orogen Biosciences, Inc., Sarasota, FL (US)

(72) Inventors: James B. Gandy, Calhoun, LA (US); Ryan N Brandt, Cape Coral, FL (US)

(73) Assignee: PGFX Patent Holdings, LLC, West Monroe, LA (US)

( * ) Notice: Subject to any disclaimer, the term of this patent is extended or adjusted under 35 U.S.C. 154(b) by 0 days.

(21) Appl. No.: 13/986,745

(22) Filed: May 31, 2013

Related U.S. Application Data

(62) Division of application No. 12/462,942, filed on Aug. 12, 2009, now Pat. No. 8,454,907.

(51) Int. Cl.
| | | |
|---|---|---|
| *G01N 1/10* | (2006.01) | |
| *C07K 1/34* | (2006.01) | |
| *B01J 3/00* | (2006.01) | |
| *G01N 33/49* | (2006.01) | |

(52) U.S. Cl.
CPC . *C07K 1/34* (2013.01); *B01J 3/006* (2013.01); *G01N 33/491* (2013.01)
USPC .......................................... 436/177; 422/527

(58) Field of Classification Search
CPC ................................................... G01N 33/491
USPC .................. 436/177, 178; 422/527, 533, 546
See application file for complete search history.

(56) References Cited

U.S. PATENT DOCUMENTS

| | | | | |
|---|---|---|---|---|
| 3,768,653 A | 10/1973 | Brumfield | ...................... | 210/188 |
| 4,479,896 A | 10/1984 | Antoniades | .................. | 260/112 |
| 4,957,742 A | 9/1990 | Knighton | ....................... | 424/532 |
| 5,028,531 A | 7/1991 | Ueda et al. | .................... | 435/69.4 |
| 5,165,928 A | 11/1992 | Smith et al. | ................. | 424/93 Q |
| 5,192,434 A | 3/1993 | Moller | ........................... | 210/227 |
| 5,192,439 A | 3/1993 | Roth et al. | ..................... | 210/485 |
| 5,304,164 A | 4/1994 | Lindsay | ......................... | 604/403 |
| 5,318,782 A * | 6/1994 | Weis-Fogh | ..................... | 424/529 |
| 5,374,257 A | 12/1994 | Drainville et al. | ............. | 604/319 |
| 5,484,428 A | 1/1996 | Drainville et al. | ............. | 604/319 |
| 5,636,643 A | 6/1997 | Argenta et al. | ................ | 128/897 |
| 5,645,081 A | 7/1997 | Argenta et al. | ................ | 128/897 |
| 5,785,682 A | 7/1998 | Grabenkort | | |

(Continued)

FOREIGN PATENT DOCUMENTS

| | | | | |
|---|---|---|---|---|
| CA | 2235272 | 4/1997 | .............. | A61M 1/00 |

OTHER PUBLICATIONS

"Luer Connector—BMEzine Encyclopedia" downloaded from wiki. bmezine.com on Jul. 31, 2009.
U.S. Appl. No. 12/459,111, filed Jul. 9, 2009, Gandy et al.

*Primary Examiner* — Paul Hyun
(74) *Attorney, Agent, or Firm* — Price & Adams

(57) ABSTRACT

A reservoir is supported by a base in a vertical position. A reciprocating member is positioned in the reservoir forming an internal chamber. The chamber receives growth factor starting material through an inlet in the reciprocating member. After the inlet is sealed, the reciprocating member increases the volume of the chamber to apply negative pressure to the growth factor starting material within the chamber to produce activated growth factors. The activated growth factors are extracted from the chamber through an outlet in the reciprocating member. Optionally, the growth factor starting material is held in the chamber to separate into fractions.

6 Claims, 6 Drawing Sheets

(56) References Cited

U.S. PATENT DOCUMENTS

| | | | |
|---|---|---|---|
| 5,785,700 A | 7/1998 | Olson | 604/408 |
| 6,010,627 A | 1/2000 | Hood, III | 210/321.6 |
| 6,071,267 A | 6/2000 | Zamierowski | 604/289 |
| 6,214,338 B1 | 4/2001 | Antanavich et al. | 424/93.72 |
| 6,303,112 B1 | 10/2001 | Worden | 424/78.06 |
| 6,508,778 B1 | 1/2003 | Verkaart et al. | 604/6.15 |
| 6,613,035 B1 | 9/2003 | Longo et al. | 604/403 |
| 6,649,072 B2 | 11/2003 | Brandt et al. | 210/782 |
| 6,964,646 B1 | 11/2005 | Biesel | 604/7 |
| 7,172,071 B2 | 2/2007 | Hawkins | 206/438 |
| 7,198,046 B1 | 4/2007 | Argenta et al. | 128/897 |
| 7,216,651 B2 | 5/2007 | Argenta et al. | 128/897 |
| 7,534,240 B1 | 5/2009 | Johnson | 604/543 |
| 7,553,306 B1 | 6/2009 | Hunt et al. | 604/543 |
| 2002/0115952 A1 | 8/2002 | Johnson et al. | 602/41 |
| 2005/0109716 A1 | 5/2005 | Leach et al. | 210/787 |
| 2006/0142707 A1 | 6/2006 | Trickett | 604/319 |
| 2007/0049739 A1* | 3/2007 | Troxel et al. | 530/399 |
| 2009/0012482 A1 | 1/2009 | Pinto et al. | 604/313 |
| 2009/0076467 A1 | 3/2009 | Pinto et al. | 604/290 |

* cited by examiner

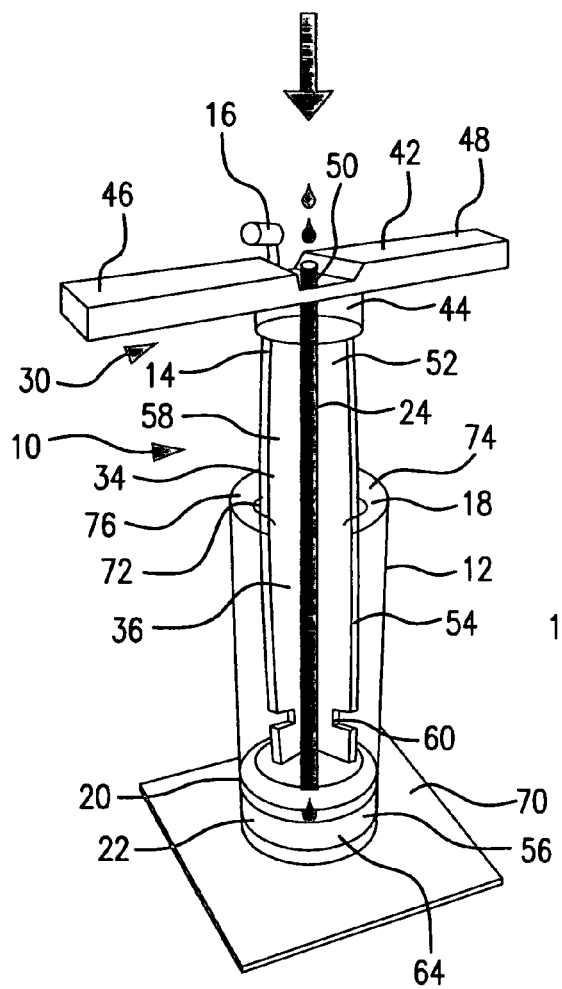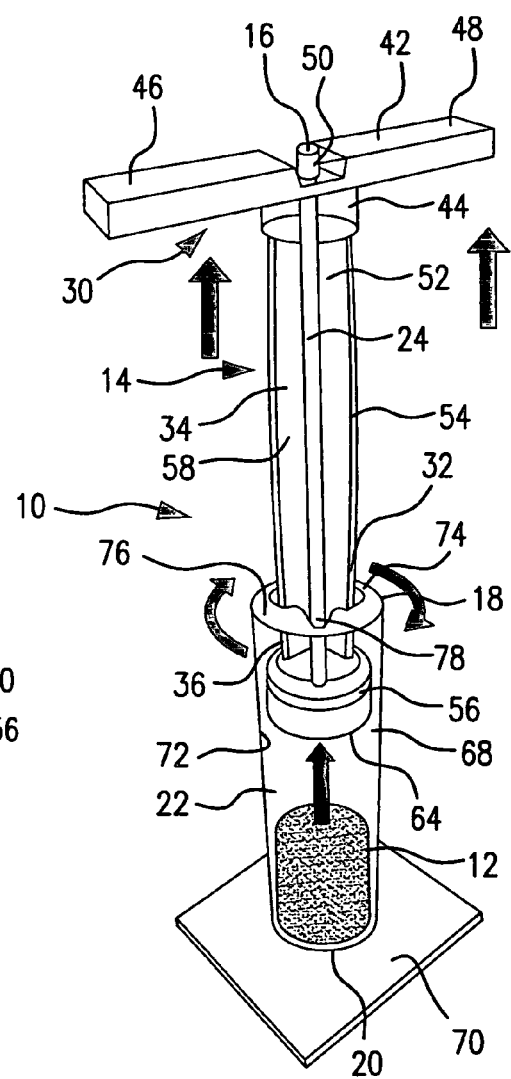
FIG.6
FIG.7

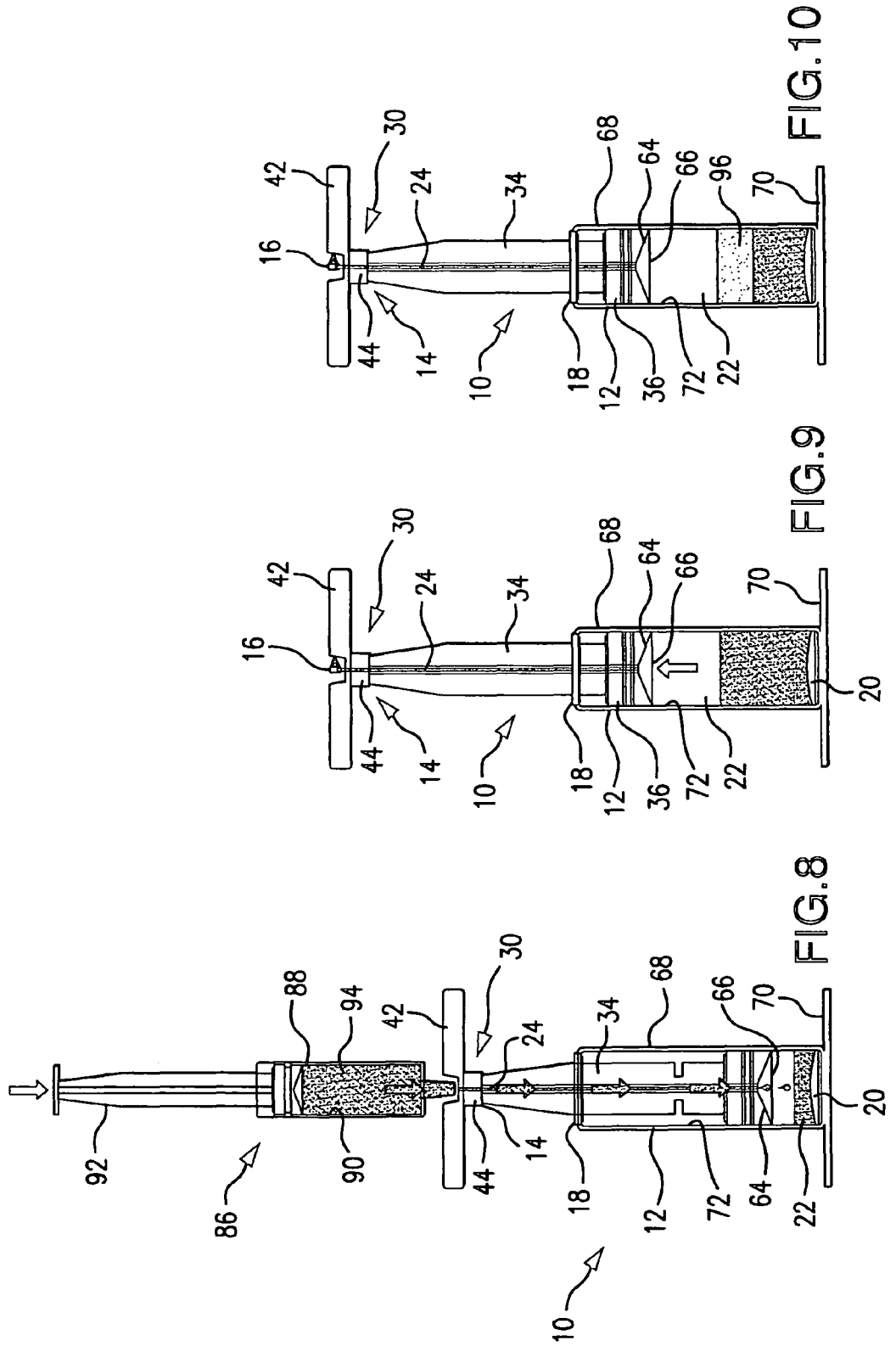

APPARATUS FOR OBTAINING GROWTH FACTORS

CROSS-REFERENCE TO RELATED APPLICATION

This application is a continuation of U.S. patent application Ser. No. 12/462,942 filed on Aug. 12, 2009, now U.S. Pat. No. 8,454,907 issued Jun. 4, 2013.

BACKGROUND OF THE INVENTION

1. Field of the Invention

The invention relates to an apparatus for extracting and isolating growth factors from platelets and, more particularly, method, apparatus, and kit for obtaining a wound healing composition of growth factors released from mammalian platelet membranes for use in wound healing and other therapeutic uses.

2. Description of the Prior Art

Various devices for collecting and utilizing blood, blood products, plasma, platelets, bone graft materials, and other similar substances are known. U.S. Pat. No. 7,172,071 discloses a method and apparatus for packaging, reconstituting, and delivering bone graft material. The device includes a first container and a second container. The first container maintains the bone graft material at a vacuum, while providing a favorable negative pressure during reconstitution. The device also reconstitutes bone graft under a negative pressure when a reconstituting liquid is injected into a container that is separated from a second container by a gas permeable membrane.

Devices for collecting blood, blood products, plasma, and platelets include devices that are used in the autologous transfusion of blood, autotransfusion systems, cardiotomy reservoirs, and other similar systems. Several patents and patent publications disclose devices or systems for collecting blood that include chambers that have the ability to communicate with vacuum sources.

U.S. Pat. No. 6,508,778 discloses a system for withdrawing blood. The system includes a rigid canister that connects to a vacuum source, a tubing set that includes a stopcock, and a source of anticoagulant that connects to the tubing set. Canadian Patent No. 2,235,722 discloses a rigid canister.

U.S. Pat. No. 6,964,646 discloses a device that is used in the autologous transfusion of blood. The device includes a collecting tank and a vacuum source that connects to the collecting tank.

U.S. Pat. No. 5,785,700 discloses an autotransfusion system including a rigid receptacle carrying a blood collection bag internally and a manually operable portable vacuum source (MOPVS) also carried by the rigid receptacle. The system may be configured in a blood collection mode wherein the MOPVS is in flow communication with the interstitial space between the collection bag and the rigid receptacle to cause a negative pressure therein to draw blood from the patient's wound. In a reinfusion mode, the MOPVS is disconnected from the rigid receptacle and is directly connected to the drain tube leading to the patient to drain unwanted fluid from the patient's wound. The rigid receptacle is inverted and connected to a transfusion line to reinfuse the blood collected within the blood collection bag. The interstitial space is vented to ambient pressure such that the blood within the collection bag is reinfused under force of gravity alone. A hydrophobic vent is connected to the flexible collection bag to vent air collected within the bag to the interstitial space.

U.S. Pat. Nos. 5,374,257 and 5,484,428 disclose a fluid collection container for collecting blood under the influence of a vacuum. The fluid collection container includes a rigid front wall and a flexible rear wall. In a distended configuration, liquid and gaseous fluid flow from the body cavity or wound being drained under the influence of vacuum into the collection container. In a collapsed configuration, the flexible rear wall is foldable relative to the rigid front wall to allow the collected liquid fluids to be reinfused to the patient.

U.S. Pat. No. 3,768,653 discloses a cardiotomy reservoir for recovering patient blood in a surgical procedure. The reservoir includes a uniform tubular case having a base plate and a top plate that provide an enclosed reservoir volume. A blood inlet conduit provides blood to the reservoir. A filtered air exit conduit allows air to flow out of the reservoir. All of the components are physiologically compatible with patient blood.

U.S. Patent Publication No. 2005/0109716 discloses a blood collection and separation system. The system has the ability to connect to a vacuum system.

U.S. Pat. No. 5,192,439 discloses a blood collection reservoir and filter device. The device connects to a vacuum source.

U.S. Pat. No. 6,613,035 discloses an autotransfusion system that includes a collection chamber and a vacuum source.

U.S. Pat. No. 5,304,164 discloses an apparatus for handling a patient's blood during a medical procedure having a reservoir.

U.S. Patent Publication No. 2006/0142707 discloses a system that is used for autologous normovolemic hemodilution. The system includes a canister that holds a bag for collecting blood. The canister includes an inlet that communicates with a vacuum source for evacuating the space between the bag and an internal wall of the canister.

Blood, blood products, plasma, platelets, and other similar substances are very important to the wound healing process. The wound healing process is generally considered to occur in several stages, generally known as the healing cascade. After tissue injury, platelets are among the first cells to appear in the vicinity of the wound. Activation of a platelet by an agonist, such as thrombin, or other agonists known in the art, leads to the release of granule material from within the platelet. Such granulation activation results in the release of proteins known as growth factors, primarily concentrated in the alpha granules of platelets. Released growth factors stimulate the formation of new tissue.

When applied to wounds, growth factors are known to increase the rate of collagen laydown, vascular ingrowth, fibroblast proliferation and overall healing. The release of a protein known as platelet-derived growth factor (PDGF) is a chemotactic signal for monocytes, neutrophils and fibroblasts which then move into the wound to begin the inflammatory stage of the healing process. During this time, monocytes secrete a number of factors, including PDGF and transforming growth factor-beta 1 (TGF-β1) (also found in platelets). In this manner fibroblasts are activated to begin the repair stage of the healing process. Subsequently, wound healing continues through the process of collagen remodeling within the wound.

The term "therapeutically effective amount" refers to the amount or amounts of the constituent bioactive elements or combination thereof necessary to enhance wound healing. Examples of wound healing include the reduction in the volume or surface area of a wound, the increase in the amount of granulation tissue or other biological material facilitating collagen laydown, vascular ingrowth, fibroblast proliferation or overall healing.

Several patents and patent applications are directed to negative pressure therapy, which utilizes growth factors that are naturally present in a wound to promote wound healing. U.S. Pat. No. 6,071,267 discloses a fluid management interface system. The system includes a subsystem that functions to extract fluids, including the patient's blood, serum, etc., from an interface system. The subsystem also introduces various fluids, such as antibiotics, analgesics and growth factors into the interface system. The system also communicates with a vacuum source.

U.S. Pat. Nos. 5,636,643, 5,645,081, 7,198,046, and 7,216,651 disclose a method for treating tissue damage with negative pressure to a wound. The method utilizes a fluid impermeable wound cover that is sealed over a wound site. A screen in the form of an open-cell foam screen or a rigid porous screen is placed between the wound cover and the wound. A vacuum pump supplies suction to the wound cover over the treatment site.

U.S. Pat. Nos. 7,534,240 and 7,553,306 disclose a method and apparatus for treating a wound using negative pressure therapy. The method and apparatus utilizes a foam pad that is in fluid communication with a vacuum source. The foam pad is predisposed with basic fibroblast growth factors or other factors.

U.S. Patent Publication No. 2002/0115952 discloses a biocompatible wound dressing that is used in negative pressure therapy. The wound dressing includes a biocompatible pad and an air-tight seal. The pad must be in fluid communication with a negative pressure source.

U.S. Patent Publication Nos. 2009/0012482 and 2009/0076467 disclose a device that is used in negative pressure therapy. The device includes a sealant layer that encloses a wound and a suction apparatus that reduces the pressure within the enclosure. Optionally, the device includes a collection chamber that is designed to collect exudate or necrotic debris.

It is known to use activated autologous platelets as a treatment in a number of medical and surgical procedures, including but not limited to oral and maxillofacial surgery, orthopedic surgery, cosmetic and reconstructive surgery, chronic tissue repair, sports medicine injuries, neurosurgery, cardiovascular surgery, podiatry, hair transplant surgery, medical research, tissue engineering, and non-surgical cellular therapy.

U.S. Pat. Nos. 4,957,742 and 6,649,072 disclose wound healing compositions that include platelet enriched plasma which prior to use is activated by thrombin to release growth factors from the alpha granules of the platelets.

Unlike negative pressure therapy, which is an in vivo process, there is some interest in extracting platelets or other similar substances for therapeutic purposes. However, extracting therapeutic levels of platelets has been a technical challenge requiring trained cardiovascular perfusionists to operate the equipment originally designed for the production of platelet rich plasma (PRP). The clinical practitioner now has access to more simplified equipment that allows him to process PRP with smaller amounts of whole blood in a shorter amount of time. Venous access, clinical expertise, and cost are still challenges that have limited the widespread use of this process throughout the world. Moreover from a commercial standpoint, wound healing compositions that include platelets must meet costly FDA guidelines applicable to blood products.

Growth factors are responsible for the wound healing process, as described above. Platelets function merely as carriers for the growth factors. Therefore, there is a need for an inexpensive and efficient process for extracting and isolating growth factors from the platelets contained in plasma for subsequent use in wound healing. The final product preferably may be free of other components that are typically found in conventional platelet enriched wound healing products, namely the platelets themselves, ghost platelets, white blood cells, red blood cells, bacteria, and other cellular debris.

It is further desirable to prepare a wound healing product that can be subjected to conventional preservations, such as lyophilization, freeze drying, and cryopreservation in a process that does not destroy the growth factors. In this manner the shelf life of the product would be prolonged.

Therefore, there is a need for a process for isolating and extracting growth factors in a non-destructive manner from platelets. The resulting composition may or may not be substantially free of other components, such as platelets, ghost platelets, white blood cells, red blood cells and bacteria, and can be used immediately fresh or lyophilized or freeze dried into a shelf-stable product for subsequent use.

SUMMARY OF THE INVENTION

In accordance with the present invention there is provided an apparatus for obtaining growth factors that includes a reservoir having an open end portion and a closed end portion. A plunger mechanism is positioned in the reservoir to define a chamber for receiving growth factor starting material between the plunger mechanism and the reservoir closed end portion. The plunger mechanism includes a lower section having a head with a tip extending outwardly on the head. The plunger mechanism is movable to selected positions within the reservoir relative to the closed end portion to increase and decrease the volume of said chamber. A throughbore extends through the plunger mechanism for communication with the reservoir. The throughbore has at one end an inlet extending out of said reservoir to receive growth factor starting material and at an opposite end an outlet extending through the head. The throughbore outlet communicates with the chamber in the reservoir closed end portion for supplying the chamber with growth factor starting material. The head tip at the plunger mechanism lower section contacts the reservoir closed end portion to minimize the volume of the chamber before the growth factor starting material is supplied to the chamber.

Further in accordance with the present invention, there is provided apparatus for extracting growth factors from growth factor starting material that includes a reservoir having an open end portion and a closed end portion. A plunger mechanism is positioned in the reservoir to define a chamber for receiving growth factor starting material between the plunger mechanism and the reservoir closed end portion. The plunger mechanism is movable to selected positions within the reservoir relative to the closed end portion. The plunger mechanism includes a lower section having a head with a tip extending outwardly on the head. A sealable throughbore extends the plunger mechanism for communication with the reservoir. The throughbore has at one end an inlet extending out of the reservoir to receive growth factor starting material and at an opposite end an outlet extending through the head. The throughbore outlet communicates with the chamber in the reservoir closed end portion for supplying the chamber with growth factor starting material. The throughbore forms a flow path through the plunger mechanism to the chamber for the injection of growth factor starting material from the inlet to the outlet of the throughbore to accumulate in the chamber and raise the plunger mechanism as the head maintains contact with the growth factor starting material.

Further in accordance with the present invention, there is provided a method for obtaining activated growth factors that includes the steps of positioning a reciprocating member in an open end of a reservoir to form a chamber below the reciprocating member within the reservoir. Growth factor starting material is injected into the chamber. The reciprocating member is moved in the reservoir to a position to increase the volume of the chamber to create negative pressure for application on the growth factor starting material to produce activated growth factors in the chamber. Activated growth factors are extracted from the chamber.

Accordingly, a principal object of the present invention is to provide a method and apparatus for releasing growth factors from growth factor starting material for use in wound healing medical procedures.

Another object of the present invention is to provide an apparatus that separates growth factors from platelets and preserves the growth factors in a concentration for improved wound healing.

Another object of the present invention is to provide an apparatus for preparing a wound healing composition that includes growth factors released from a starting material in a bioactive state for enhancing tissue growth.

A further object of the present invention is to provide a method that utilizes an apparatus for releasing growth factors from growth factor starting material for use in wound healing medical procedures.

A further object of the present invention is to provide a kit for releasing growth factors from growth factor starting material for use in wound healing medical procedures.

These and other objects of the present invention will be more completely disclosed and described in the following specification, accompanying drawings, and appended claims.

BRIEF DESCRIPTION OF THE DRAWINGS

FIG. 6 is a fragmentary isometric view of the assembled extractor shown in FIG. 1, illustrating the flow of blood into the assembled extractor.

FIG. 7 is a fragmentary isometric view similar to FIG. 6, illustrating reciprocal movement of a plunger in the assembled extractor to expand the volume of an internal chamber to create negative pressure therein.

FIG. 8 is a sectional view in side elevation of the assembled extractor, illustrating the injection of blood into the assembled extractor from a syringe.

FIG. 9 is a sectional view in side elevation of the assembled extractor, illustrating the raising of a plunger within the assembled extractor to create negative pressure in a chamber to activate growth factors in the blood in the chamber.

FIG. 10 is a sectional view in side elevation of the assembled extractor, illustrating the separation of platelet rich plasma (PRP) from red blood cells within the extractor due to gravity.

DESCRIPTION OF THE PREFERRED EMBODIMENTS

Figure 1:
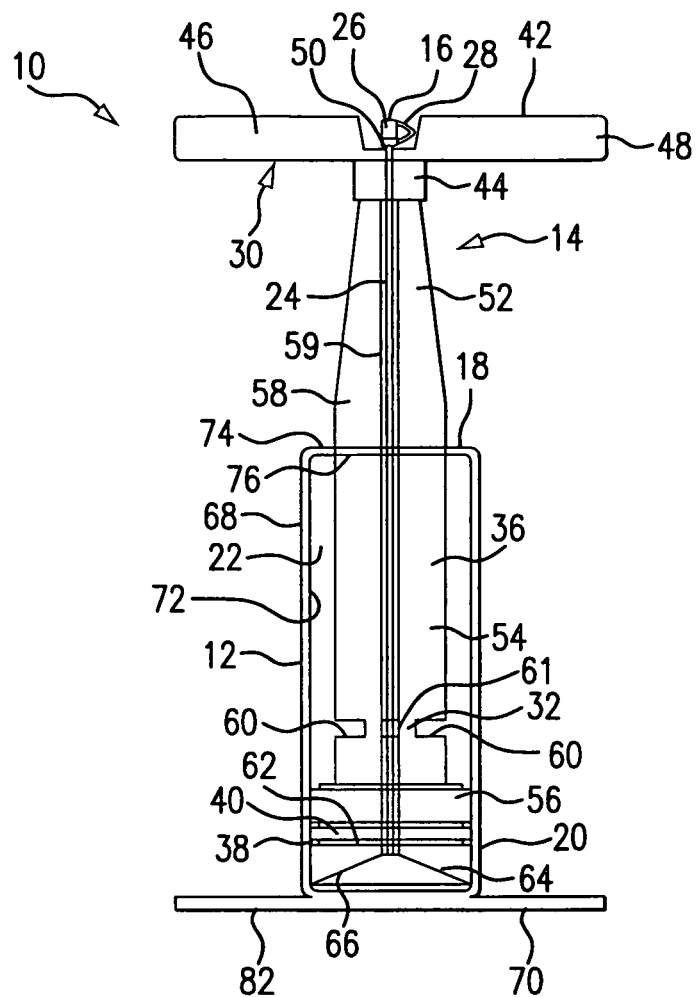
FIG. 1 is a sectional view in side elevation of an assembled extractor.

Referring to the drawings and particularly to FIGS. 1-5, there is shown an assembled extraction apparatus or extractor generally designated by the numeral 10. The extractor receives a quantity of growth factor starting material and subjects the growth factor starting material to negative pressure or a vacuum to activate the growth factors therein. Once the growth factors have been activated, the growth factors are removed from the extractor 10, as shown in FIGS. 8-12. Optionally, the extractor 10 uses gravity to separate the growth factor starting material into fractions with at least one of the fractions including the activated growth factors.

The extractor 10 is particularly adapted for use in a process for removing growth factors from a growth factor starting material, such as the process that is disclosed in pending U.S. patent application Ser. No. 12/459,911, which is incorporated herein by reference. The growth factor starting material preferably includes platelets for subsequent use in wound healing, either alone or in combination with other wound healing components. With known prior art methods, platelet concentrated plasma products are prepared through multistep processes and then subsequently activated with thrombin or collagen prior to use to release the growth factors from the platelets' alpha granules. In contrast, the process of the present invention allows for the separation of growth factors from concentrated platelets without the need to use thrombin for activation. Consequently, fewer steps are required to isolate the growth factors. After the separation process, the growth factors are released in a bioactive state in a nondestructive medium, such as plasma, sterile water, saline, and the like. In a bioactive state the released growth factors have a positive reaction on living tissue and enhanced wound healing.

As used herein, growth factor refers to any material or materials having a positive reaction on living tissues, such as promoting the growth of tissues. Exemplary growth factors include, but are not limited to, platelet-derived growth factor (PDGF), platelet-derived angiogenesis factor (PDAF), vascular endotheial growth factor (VEGF), platelet-derived epidermal growth factor (PDEGF), platelet factor 4 (PF-4), transforming growth factor beta. (TGF-B), acidic fibroblast growth factor (FGF-A), basic fibroblast growth factor (FGF-B), transforming growth factor A (TGF-A), insulin-like growth factors 1 and 2 (IGF-1 and IGF-2), B thromboglobulin-related proteins (BTG), thrombospondin (TSP), fibronectin, von Wallinbrand's factor (vWF), fibropeptide A, fibrinogen, albumin, plasminogen activator inhibitor 1 (PAI-1), osteonectin, regulated upon activation normal T cell expressed and presumably secreted (RANTES), gro-A, vitronectin, fibrin D-dimer, factor V, antithrombin III, immunoglobulin-G (IgG), immunoglobulin-M (IgM), immunoglobulin-A (IgA), a2-macroglobulin, angiogenin, Fg-D, elastase, keratinocyte growth factor (KGF), epidermal growth factor (EGF), fibroblast growth factor (FGF), tumor necrosis factor (TNF), fibroblast growth factor (FGF) and interleukin-1 (IL-1), Keratinocyte Growth Factor-2 (KGF-2), and combinations thereof. One of the important characteristics common to the above listed growth factors is that each substance is known or believed to have a positive reaction on living tissue, known as bioactivity, to enhance cell or tissue growth.

It should be understood herein that growth factor starting materials include, but are not limited to, platelets, platelet rich plasma, whole blood, bone marrow, umbilical cord fluid and combinations thereof. For improved clinical use of growth factors, it is important that the growth factor starting material not be frozen prior to separation of the growth factors from platelets. Preferably, all embodiments of the present invention are assumed to produce at least therapeutically effective amount(s) of constituent substances or combinations thereof to possess the above positive bioactive properties. The processes for obtaining the growth factors should be performed above freezing temperatures, preferably room temperature.

Figure 2:
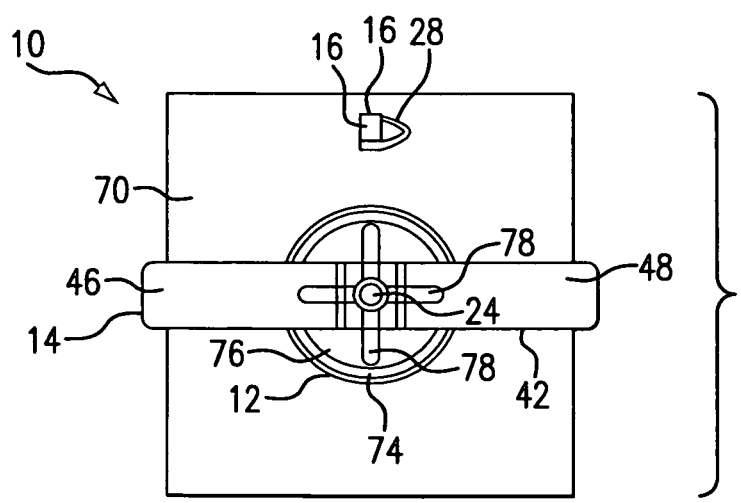
FIG. 2 is a top plan view of the assembled extractor shown in FIG. 1.

As shown in FIGS. 1-2, the extractor 10 includes a container or reservoir 12, an essentially t-shaped reciprocating member 14, and a removable cap 16. The reservoir 12 has an open end portion 18 and a closed end portion 20. The reciprocating member 14 inserts into the open end portion 18 to move back and forth relative to the closed end portion 20 within the reservoir 12. The reciprocating member 14 and the reservoir closed end portion 20 define a chamber 22 of varying volume within the reservoir 12.

The reciprocating member 14 includes a throughbore 24 that serves as a sealable inlet for introducing growth factor starting material into the extractor 10. The throughbore 24 extends through the reciprocating member 14 vertically to communicate with the reservoir 12 so that the growth factor starting material flows through the reciprocating member 14 into the chamber 22. The throughbore 24 also facilitates aspiration of the chamber 22.

Once growth factor starting material is inserted into the chamber 22, the cap 16 is positioned on the reciprocating member 14 to close the throughbore 24 to seal the chamber 22. The cap 16 includes a cap portion 26 to cover the throughbore 24 in a sealed position. The cap 16 also includes a retaining line or tether 28 that connects the cap 16 to the extractor 10 when the cap 16 is not in a sealed position.

As shown in FIGS. 1-2, a device generally designated by the numeral 30 moves the reciprocating member 14 to a predetermined position within the reservoir 12 to increase the volume of the sealed chamber 22. The extractor 10 includes a locking mechanism 32 that holds the reciprocating member 14 in the predetermined position to act as a petcock. Preferably, the device 30 raises the reciprocating member 14 vertically to increase the volume of the sealed chamber 22. As shown in FIG. 2, once the device 30 raises the reciprocating member 14 to a predetermined height, the device 30 rotates the reciprocating member 14 to engage the locking mechanism 32.

In the raised position, the device 30 applies a negative pressure to the growth factor starting material within the sealed chamber 22, which produces activated growth factors therein. The activated growth factors remain in the growth factor starting material until they are extracted from the reservoir 12.

As shown in FIGS. 1-2, the throughbore 24 also functions as an outlet to facilitate removal of the activated growth factors from the extractor 10. The throughbore 24 communicates with the chamber 22 to allow activated growth factors to flow from the reservoir 12 through the reciprocating member 14 after the cap 16 has been removed to unseal the chamber 22. In the preferred embodiment, a predetermined fraction of the growth factor starting material having the activated growth factors therein is removed for a specific application with the remaining fractions being used in other applications or being discarded.

Figure 3:
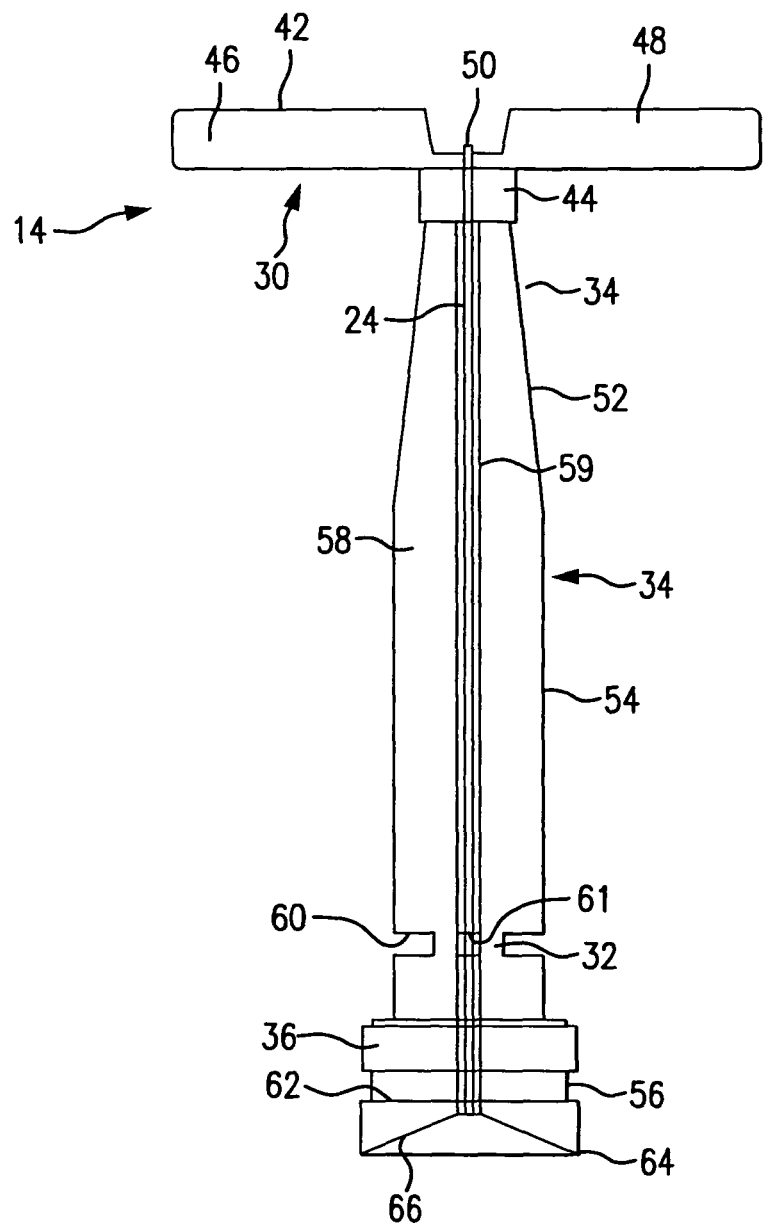
FIG. 3 is a sectional view in side elevation of a plunger for use in the assembled extractor shown in FIG. 1.

Referring to FIGS. 1-3, the reciprocating member 14 includes a plunger mechanism 34 and the device 30. The plunger mechanism 34 has an elongated plunger 36 that frictionally engages the reservoir 12. The plunger mechanism 34 also includes a groove 38 that receive an o-ring 40 shown. The o-ring 40 maintains the seal within the reservoir 12.

Referring to FIG. 3, the device 30 includes a handle 42 that applies a force to raise or lower the reciprocating member 14 within the reservoir 12. The throughbore 24 extends vertically through the handle 42 and the plunger mechanism 34 to communicate with the reservoir 12.

The reciprocating member 14 includes the integrally connected handle 42 and plunger mechanism 34. In the preferred embodiment, the handle 42 and the plunger mechanism 34 are formed separately and are connected integrally and permanently through conventional joining processes. Alternatively, the handle 42 and the plunger mechanism 34 are formed as a single unit.

The handle 42 is a tee handle having an essentially cubic tubular center section 44 that connects to the plunger mechanism 34 and a pair of essentially flat wings 46, 48 that extend outwardly from the center section 44 to facilitate gripping of the handle 42. The center section 44 is recessed relative to the wings 46, 48.

As shown in FIG. 3, the center section 44 includes an essentially cylindrical, tubular projection 50 that extends upwardly from the handle 42. The throughbore 24 extends downwardly through the tubular projection 50 and the handle 42 to communicate with the plunger mechanism 34. The tubular projection 50 includes a conventional connecting mechanism that connects to the cap 16 shown in FIGS. 1-2. Preferably, the cap portion 26 includes a male luer lock connector for inserting into a female luer lock connector in the tubular projection 50 to connect the cap 16 to the handle 42 and seal the throughbore 24.

Once the cap 16 connects to the handle 42 to seal the throughbore 24, the handle 42 has the ability to move the plunger mechanism 34 in a vertical direction to expand the volume of the chamber 22 in the reservoir 12 in the FIGS. 1-2. The handle 42 raises the plunger mechanism 34 to increase the volume of the chamber 22 and lowers the plunger mechanism 34 to decrease the volume of the chamber 22. When the chamber 22 is sealed, the increase in the volume of the chamber 22 applies negative pressure to activate growth factors within the growth factor starting material held in the chamber 22.

The movement of the handle 42 and the plunger mechanism 34 is generated through any manual or motorized source (not shown). Preferably, the movement of the plunger mechanism 34 is facilitated through manual manipulation of the handle 42.

As shown in FIG. 3, the plunger mechanism 34 includes a tapered upper section 52, a middle section 54, and an essentially disc-shaped lower section 56. The throughbore 24 extends through the upper section 52, the middle section 54, and the lower section 56 to communicate with reservoir 12 shown in FIGS. 1-2.

As shown in FIG. 3, the upper section 52 and the middle section 54 of the plunger mechanism 34 are formed from a pair of essentially flat plates or bars 58, 59 that intersect one another perpendicularly manner to form an essentially x-shaped or crossed horizontal cross section. Each bar 58, 59 includes a pair of slots 60, 61 that form part of the locking mechanism 32 shown in FIG. 1.

As shown in FIG. 3, the plunger member lower section 56 includes a disc 62 that forms a head on the plunger 36 and a tip 64 that extends outwardly from an extreme end of the plunger 36. The o-ring 40 shown in FIG. 1 is positioned above the disc 62. The o-ring 40 and the plunger tip 64 maintain a seal as the disc 62 moves vertically within the reservoir 12.

As shown in FIG. 3, the tip 64 includes an essentially inverted dome shaped, concave recess 66 that communicates with the throughbore 24 and the reservoir 12. In the preferred embodiment, the concave shape of the recess 66 facilitates the extraction of a preferred fraction of the growth factor starting material that includes the activated growth factors.

Figure 4:
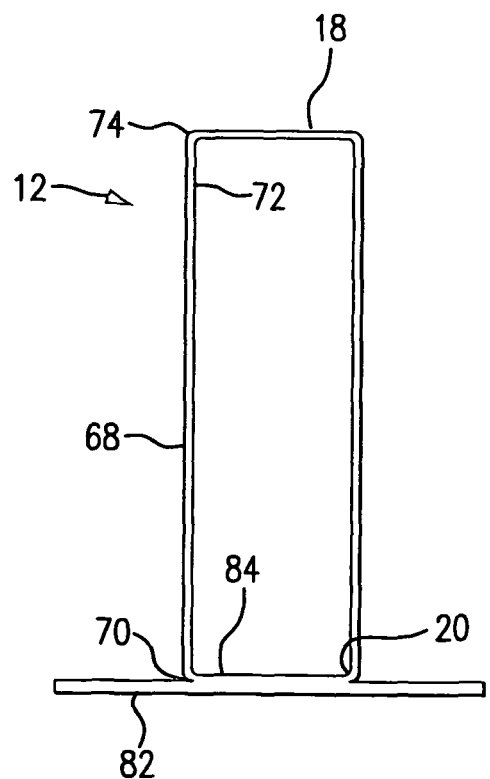
FIG. 4 is a sectional view in side elevation of a reservoir for use in the assembled extractor shown in FIG. 1.
Figure 5:
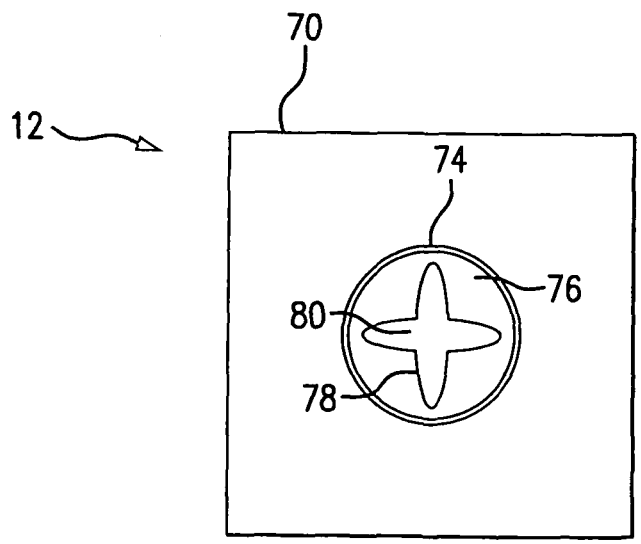
FIG. 5 is a top plan view of the reservoir shown in FIG. 4.

Referring now to FIGS. 4-5, there is shown the reservoir 12 that is used in the extractor 10 shown in FIGS. 1-2. The reservoir 12 has an elongated body 68 extending from the open end 18 to the closed end 20 and a mount 70 projecting outwardly from the closed end 20. The mount 70 provides means for holding the reservoir 12 in a fixed position to provide support and stabilization.

As shown in FIG. 4, the reservoir body 68 is essentially cylindrical and tubular with a cavity or receptacle 72 extending from the open end 18 essentially to the closed end 20. The body 68 has an essentially constant outer diameter along its length and the cavity has an essentially constant inner diameter.

As shown in FIG. 5, the reservoir open end 18 includes an essentially flat, circular disc-shaped edge 74 that retains the reciprocating member 14, shown in FIGS. 1-2, in the receptacle 72. The edge 74 prevents the reciprocating member 14 from sliding out of the receptacle 72 to prevent the spillage of blood from the reservoir 12.

The edge 74 is connected to the reservoir body 68 through conventional connection methods. Preferably, the edge 74 is integrally and permanently connected to the reservoir body 68. In such a connection, the edge 74 is formed by connecting a separately formed disc 76 through conventional permanent connecting methods, such as sonic welding, so that the reservoir and the reciprocating member 14 are provided in their assembled form.

As shown in FIG. 5, the edge 74 includes a plurality of mating slots 78 that project outwardly from a central bore 80. The slots 78 form an x-shaped pattern in the disc 76 that form part of the locking mechanism 32 shown in FIGS. 1-2. The slots 78 allow for the rotation of the plunger 36 to lock the reciprocating member 14 in a predetermined position to apply a constant negative pressure to growth factor starting material in the chamber 22 to activate growth factors.

As shown in FIG. 5, the mount 70 is essentially a thin platform or base that extends outwardly from the reservoir body 68. The mount 70 stabilizes the reservoir 12 in an essentially vertical position to allow growth factor starting material to separate under the influence of gravity.

The configuration and structure of the mount 70 are not critical, but the mount 70 must provide sufficient surface for gripping the reservoir 12, frictionally engaging the reservoir 12, holding the reservoir 12 in a stable or fixed position, or a combination thereof. As shown in FIG. 5, preferably, a lower surface 82 of the mount 70 is essentially flat to provide stability when placed on flat surfaces and the mount 70 is integral to the body 68. Alternatively, the mount 70 is a separate piece that includes locking means (not shown) that holds the body 68 in a fixed position.

As shown in FIG. 4, the reservoir closed end portion includes an inner surface 84 that is positioned within the receptacle 72. The inner surface 84 contacts the recess 66 in the plunger tip 64 shown in FIGS. 1-4 to minimize the volume of the chamber 22 before growth factor starting material is injected therein.

In operation as shown in FIGS. 6-7, the extractor 10 is positioned in an essentially vertical position with the base 70 supporting the reservoir 12 and the cap 16 removed from the throughbore 24. Growth factor starting material is injected into the throughbore 24 and flows through the reciprocating member 14 into the reservoir chamber 22. The flow of the growth factor starting material into the chamber 22 raises the reciprocating member 14 with the tip 64 maintaining contact with a pool of the growth factor starting material.

Once the chamber 22 is full, the cap 16 is placed on the throughbore 24 to seal the chamber 22. The handle 42 raises the plunger 36 to move the reciprocating member 14 within the reservoir receptacle 72. The movement of the reciprocating member 14 increases the volume of the chamber 22 to create negative pressure within the chamber 22.

The handle 42 moves the plunger 36 to a predetermined height. Once the plunder 36 reaches the predetermined height, the handle 42 rotates the plunger 36 to lock the reciprocating member 14 in a fixed position with the locking mechanism 32 to fix the volume of the sealed chamber 22. Once the reciprocating member 14 is locked in place, the growth factor starting material is subjected to a constant negative pressure or vacuum to produce activated growth factors.

The activated growth factors are produced from any suitable growth factor starting material. Preferably, the growth factor starting material includes platelets and plasma, so that the negative pressure within the chamber 22 separates or releases the growth factors from the platelets in the growth factor starting material into the plasma. The activation process leaves the platelets intact.

Suitable growth factor starting materials include a composition of platelet rich plasma (PRP) and platelet poor plasma (PPP), as described in U.S. Pat. No. 6,649,072 (hereinafter referred to as the '072 patent. The composition disclosed in the '072 patent is a 3:1 ratio of PRP to PPP.

Other exemplary platelet plasma products that are suitable for use with the extractor 10 are disclosed in U.S. Pat. Nos. 6,214,338, 6,010,627, 5,165,928, 6,303,112, and 6,649,072. The more concentrated the plasma is with platelets, the greater the concentration of growth factors that can be obtained via the present invention.

The negative pressure created by the reciprocating member 14 pulls the growth factors out of the platelets and into the plasma. The separated growth factors are mixed with a medium that is not destructive to the growth factors in a bioactive state to promote tissue growth. The platelets also remain for therapeutic use.

Optionally, the growth factor starting material is subjected to gravitational separation within the chamber 22. The gravitation separation process causes sedimentation to create multiple fractions within certain growth factor starting materials. Preferably, the gravitational separation occurs for at least 30 minutes or more.

Optionally, the growth factors are preserved for future bioactive use by preservation methods, such as lyophilization, freeze drying and cryopreservation. For example, the resulting vacuumed plasma product comprising growth factors and empty platelets are preserved via conventional methods, such as lyophilization, freeze drying and cryopreservation. In this manner a shelf-stable product is produced that is usable for several days or even months to years after preparation. When desired for use, the freeze-dried product is reconstituted with sterile 0.9% normal saline solution.

The growth factor starting material that includes the activated growth factors may be used immediately or lyophilized or freeze dried for future use. In accordance with another embodiment of the present invention, the activated growth factors are obtained from the extracted product using a 0.2 micron filter. The filtered composition contains growth factors substantially free of platelets, ghost platelets, bacteria, red blood cells, white blood cells, and cellular debris.

A preferred filter is one having a porosity of 0.2 microns or less. By filtering the vacuumed product, the released growth factors are free of cellular debris, platelet membranes, ghost platelets, white blood cells, bacteria, and red blood cells.

Growth factors preserved as above described are reconstituted or hydrated in one method using sterile 0.9% normal saline solution. The preserved product is also reconstituted using deionized water, sterile water, other liquid media or bodily fluids including, but not limited to, plasma, hemoconcentrated plasma, whole blood, bone marrow aspirate, antibiotics or any combination thereof.

In another example of the present invention, 3 milliliters of the preserved product containing about 70% growth factors is reconstituted with about 3 milliliters of 0.9% normal saline or similar liquid media, as discussed above. For wound healing purposes, a therapeutically effective amount of the reconstituted product is applied topically to cover the wound. It may also be injected at a location of soft tissue injury. Beyond wound healing, the fresh product and reconstituted product is useful in medical research applications, such as culturing out stem cells. The reconstituted product may also be a liquid product containing protein-bound growth factors not previously lyophilized.

Prior to preserving the isolated growth factors, in another process various pharmaceutical agents are added to the composition. Preferably, these agents aid in the bioactivity of wound healing and in the treatment/prevention of infection. The agents include antibiotics, antifungal agents, and the like. However, as known in the art, any number of other pharmaceutical agents may be employed. The quantity and type of agent selected must be stable in such products and be capable of withstanding lyophilization and other methods of preserving the wound healing product of the present invention.

In a further embodiment of the present invention, a bodily fluid, such as blood or an antibiotic, is used to reconstitute the final preserved product. This final product allows the clinician a wide berth of options on how it is used. In another example, a practitioner adds bone marrow aspirate and stem cells to the final product so that the patient will achieve benefits from both therapies. Additionally, a practitioner can administer the final product with an antibiotic solution at a specific anatomical site for wound healing and the like. Further, the lyophilized final product and a thrombin solution are combined to initiate a clot to be placed in a desired location to promote tissue growth.

Referring now to FIGS. 8-12, a series of steps for extracting PRP containing activated growth factors or cytokines from blood using the extractor 10 is illustrated. The extractor 10 is positioned in an essentially vertical position with the base 70 supporting the reservoir 12. A syringe 86 is aligned essentially in an overlying relationship with extractor 10, while the cap 16 is removed from the throughbore 24.

As shown in FIG. 8, the syringe 86 includes a reservoir 88 having an internal cavity 90 and a plunger 92. The plunger 92 inserts into the cavity 90 for reciprocal movement therein. The plunger 92 and the reservoir 88 define a chamber 94 for holding a quantity of blood for injection into the extractor 10. Preferably, the quantity of blood is between 40 ml and 50 ml.

The syringe 86 connects to the luer lock in the handle center section 44 to engage the extractor 10. The plunger 92 is depressed to force blood to flow from the chamber 94 through the reservoir 88 into the inlet in the throughbore 24.

As shown in FIG. 8, the blood flows along a flowpath through the handle 42 and the plunger mechanism 34 to accumulate in the chamber 22. The accumulation of blood in the chamber 22 raises the reciprocating member 14, as the tip 64 maintains contact with the blood. Once the chamber 22 receives a predetermined amount of blood, the chamber 22 is sealed by placing the cap 16 on the throughbore 24. Preferably, the reservoir 12 includes a fill line indicating the preferred amount of blood that is used in the extraction process.

As shown in FIG. 9, the handle 42 is raised to increase the volume of the chamber 22. The handle 42 raises the plunger 36 to move the reciprocating member 14 within the reservoir receptacle 72. The movement of the reciprocating member 14 increases the volume of the chamber 22 to create negative pressure for application on the blood. The negative pressure separates growth factors from the platelets within the blood to produce activated growth factors. The activated growth factors diffuse into the blood plasma.

As shown in FIG. 10, the blood is held in the chamber 22 for a predetermined period of time to allow the blood to separate into fractions 96, 98 with the assistance of gravity. One of the fractions 96 includes PRP and activated growth factors. The other fraction 98 includes red blood cells and, optionally, activated growth factors. The fractions 96, 98 have an essentially equal volume with the PRP fraction 96 occupying from 40% to 60% of the volume and the red blood cell fraction 98 essentially occupying the remainder of the volume.

After the blood is sufficiently separated into the fractions 96, 98, the cap 16, shown in FIG. 8, is removed from the throughbore 24 to unseal the chamber 22. The reciprocating member 14 is released to move downwardly until the plunger tip 64 contacts the PRP fraction 96.

Figure 11:
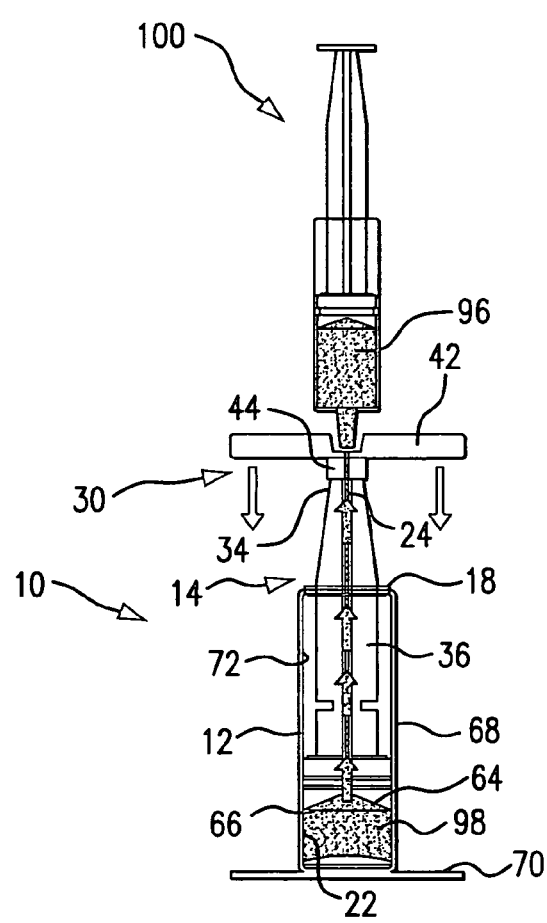
FIG. 11 is a sectional view in side elevation of the assembled extractor, illustrating the extraction of a PRP fraction containing activated growth factors from the assembled extractor using a syringe.

As shown in FIG. 11, a second syringe 100 is aligned in an overlying relation with the extractor 10. The syringe 100 connects to the luer lock within the handle center section 44. The handle 42 is depressed to reduce the volume of the chamber 22 to force the PRP and activated growth factors in the fraction 96 to flow through the throughbore 22 into the syringe 100. The configuration of the recess 66 on the plunger tip 64 directs the PRP into the throughbore 22 to prevent or to minimize the amount of the red blood cell fraction 98 that re-mixes with the PRP fraction 96.

As shown in FIG. 11, the syringe 100 continues to fill with the PRP and the activated growth factors in the fraction 96 until a predetermined quantity is obtained. Once the syringe 100 is sufficiently full, the syringe 100 disconnects from the extractor 10. A quantity of 3 ml of the PRP fraction 96 can be obtained in as little as 10 min. utilizing this method.

Figure 12:
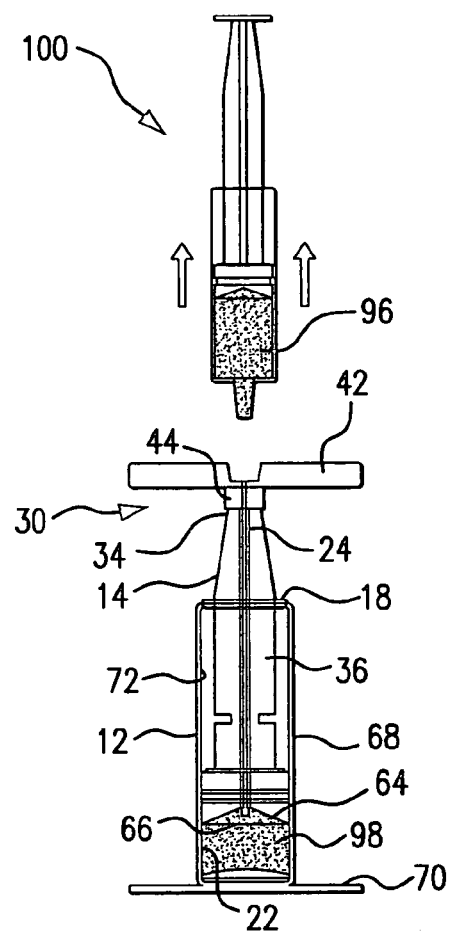
FIG. 12 is an exploded sectional view in side elevation illustration of the assembled extractor, the separation of a syringe from the assembled extractor following the extraction of the PRP fraction.

As shown in FIG. 12, the fraction 98 that includes the red blood cells and, optionally, a quantity of activated growth factors, remains in the chamber 22. Preferably, the fraction 98 is discarded. Optionally, the fraction 98 is extracted for use in wound treatment.

As shown in FIGS. 8-12, the extractor 10 is provided in a kit in an assembled or partially assembled form with the reservoir 12, the reciprocating member 14, and the cap 16. Optionally, the kit includes the syringes 86, 100.

The reservoir 12, the reciprocating member 14, and the cap 16 are formed from any suitable material utilizing any suitable fabrication or manufacturing process. All of the components must include, at least, one or more surfaces that are physiologically compatible with one or more of the growth factor starting materials. Preferably, the reservoir 12, the reciprocating member 14, and the cap 16 are formed from plastic with the reservoir 12 including a transparent or translucent portion to facilitate the viewing of the growth factor starting material in the receptacle 72. Preferably, the plastic includes polypropylene that has been approved for use in medical devices by the Federal Drug Administration.

It should be understood that while the preferred embodiment is illustrated with a throughbore that serves as a single inlet for growth factor starting material and an outlet for extracting activated growth factors, alternate embodiments are contemplated in which the extractor includes an inlet for receiving the growth factor starting material that is separate from an outlet for extracting the activated growth factor starting material. Alternate embodiments are also contemplated in which a tube that is made from flexible or rigid material extends from the handle to the plunger tip in place of the throughbore that extends through the reciprocating member.

According to the provisions of the patent statutes, we have explained the principle, preferred construction and mode of operation of our invention and have illustrated and described what we now consider to represent its best embodiments. However, it should be understood that, within the scope of the appended claims, the invention may be practiced otherwise than as specifically illustrated and described.

We claim:

1. A method for obtaining activated growth factors comprising the steps of:
   positioning a reciprocating member in an open end of a reservoir to form a chamber below the reciprocating member within the reservoir,
   injecting growth factor starting material into the chamber,
   sealing the chamber after the growth factor starting material is injected into the chamber,
   moving the reciprocating member in the reservoir to a position to increase the volume of the chamber to create negative pressure for application on the growth factor starting material to produce activated growth factors therein, and
   extracting activated growth factors from the chamber.

2. A method as set forth in claim 1 which includes:
   allowing the growth factor starting material to separate into fractions before extracting activated growth factors from the chamber.

3. A method as set forth in claim 1 which includes:
   supporting the reservoir in a fixed vertical position to facilitate gravitational separation of the activated growth factors within the growth factor starting material.

4. A method as set forth in claim 1 which includes:
   injecting growth factor starting material in an inlet of a bore extending through the reciprocating member into the chamber,
   sealing the inlet to the reciprocating member after the growth factor starting material is injected into the chamber, and
   applying negative pressure to the growth factor starting material after the chamber is sealed to release growth factors from the growth factor starting material.

5. A method as set forth in claim 1 which includes:
   locking the reciprocating member in a fixed position in the reservoir after the reciprocating member is moved to fix the volume of the sealed chamber and applying negative pressure to the growth factor starting material.

6. A method as set forth in claim 1 which includes:
   selectively separating a fraction of the growth factor starting material that contains activated growth factors therein.

* * * * *